United States Patent
An (10) Patent No.: US 8,192,198 B2
(45) Date of Patent: Jun. 5, 2012

(54) SQUEEZING GUN FOR TWO-PART MEDICAL VISCOUS FLUID

(75) Inventor: Im Jun An, Busan (KR)

(73) Assignee: Seil Global Co., Ltd., Busan (KP)

( * ) Notice: Subject to any disclaimer, the term of this patent is extended or adjusted under 35 U.S.C. 154(b) by 246 days.

(21) Appl. No.: 12/631,982

(22) Filed: Dec. 7, 2009

(65) Prior Publication Data
US 2010/0143864 A1 Jun. 10, 2010

(30) Foreign Application Priority Data
Dec. 9, 2008 (KR) .................. 10-2008-0124824

(51) Int. Cl.
*A61M 31/00* (2006.01)
*B67D 5/52* (2006.01)

(52) U.S. Cl. .......... 433/89; 604/191; 222/135; 222/333; 222/390

(58) Field of Classification Search ............. 433/89; 604/191; 222/135, 326, 333, 386, 390
See application file for complete search history.

(56) References Cited

U.S. PATENT DOCUMENTS

| 5,450,988 | A | 9/1995 | Jerdee | |
|---|---|---|---|---|
| 5,762,239 | A * | 6/1998 | Cossette | 222/326 |
| 6,488,180 | B1 * | 12/2002 | Bayat | 222/137 |
| 6,540,113 | B2 | 4/2003 | Gardos | |
| 6,619,508 | B2 * | 9/2003 | Kuczynski et al. | 222/136 |
| 7,637,392 | B2 * | 12/2009 | Hsu et al. | 222/137 |
| 2004/0039368 | A1 * | 2/2004 | Reilly et al. | 604/500 |

* cited by examiner

*Primary Examiner* — Ralph Lewis
(74) *Attorney, Agent, or Firm* — Jordan and Hamburg LLP (57) ABSTRACT

A squeezing gun for two-part medical viscous fluid that simultaneously squeezes two different kinds of medical viscous fluid contained in a double cartridge including two tubes containing the respective different kinds of fluids. Two horizontal scroll bars are moved horizontally to actuate the squeezing of the fluids and are driven by a driving motor.

1 Claim, 8 Drawing Sheets

SQUEEZING GUN FOR TWO-PART MEDICAL VISCOUS FLUID

BACKGROUND OF THE INVENTION

1. Field of the Invention

This invention is about squeezing gun for two-part medical viscous fluid that extrudes two different kinds of medical viscous fluid at the same time that are contained in double cartridge where two tubes are combined into one body and when explained in more detail, this invention is to extrude simultaneously two kinds of medical viscous fluid (hereinafter call viscous fluid) that are contained in double cartridge while two horizontal scroll bars are moving horizontally as driving power of driving motor is being reduced when button of squeezing gun which has the shape of pistol is pushed.

2. Description of the Prior Art

Existing squeezing gun for two-part medical viscous fluid has had the shape of pistol overall and in the case that users squeeze viscous fluid in double cartridge which has been installed in cartridge insertion edge of squeezing gun, users should squeeze simultaneously two different kinds of viscous fluid contained in double cartridge by first pulling a trigger and then two horizontal scroll bars moving forward horizontally.

Double cartridge mentioned above contains two tubes which are combined in one body and two different kinds of viscous fluid are contained in the two tubes respectively and viscous fluid contained in double cartridge is gel type which has high and stiff viscosity and the viscous fluid is used to mold from the tooth when putting crown on tooth in dentistry.

It has been difficult for user to squeeze viscous fluid with high viscosity by only the power of index finger and squeezing requires considerable power. Besides, viscous fluid has not been squeezed correctly in the position that is intended to be targeted because edge of double cartridge is shaken from which viscous fluid is squeezed.

SUMMARY OF THE INVENTION

This invention is to solve the problem mentioned above. This invention has the technological project to solve the problem as follows. First, stiff viscous fluid in double cartridge can be squeezed easily by only a little power that presses push button that supplies power to driving motor by enabling horizontal scroll bar to be moved horizontally with electric power of driving motor where decelerator is installed. Second, viscous fluid can be injected conveniently in the position that is targeted by detaching double cartridge from squeezing gun easily.

The feature of this invention to achieve the purpose mentioned above can be summarized as follows.

Case main body whose forward area is open is installed at the upper side of handle where push button is installed. The open forward area of case main body is formed by cartridge insertion parts where rear area flange part of double cartridge in which a pair of tubes that are filled with different viscous fluid is inserted and fixed. A pair of horizontal scroll bars that move forward when push button is pressed is installed in the case main body. Screw thread is formed around all outer circumference edges of horizontal scroll bar and key way is formed in horizontal scroll bar throughout the length in transverse direction and a pair of horizontal scroll bars mentioned above are protruded backward through holes that are formed on rear wall of housing and the rear side of horizontal scroll bars of both sides which is protruded backward is installed so that the rear side can be supported by bracket. Springs that move horizontally scroll bars of both sides backward are installed in guide pin that is installed between rear wall and bracket and driving motor which is equipped with decelerator is installed in the case main body and driving gear is installed on the axis of rotation of decelerator. A pair of horizontal scroll bars penetrates the case main body and housing whose driving gear is exposed forward is installed in the case main body. Gear body of rotation which engages driving gear is installed in both sides of housing and protruded key that is directed to key way of tube type main body that is inserted outside of horizontal scroll bar and that enables device to move vertically is formed inside of gear body of rotation. In squeezing gun for two-part medical viscous fluid which is made up of final gear engages driving gear, screw holes which correspond to screw threads of horizontal scroll bar are formed in both sides of a pair of horizontal scroll bar which is located in the housing mentioned above. A pair of clutches which form slope part outside with springs interposed are installed elastically. Cover which forms two clutch adhesion parts that close up a pair of clutches is installed in the open forward upper side of housing mentioned above in hinged mode.

This invention regarding squeezing gun for two-part medical viscous fluid has the advantage in squeezing stiff viscous fluid in double cartridge easily by a little power that presses push button of switch shape which supplies power to driving motor by enabling horizontal scroll bar to be moved horizontally with electric power of driving motor where decelerator is installed.

Besides, this invention enables viscous fluid to be injected correctly to the targeted place by easily detaching double cartridge from squeezing gun as horizontal scroll bar can be retracted rapidly due to elasticity of spring when opening cover installed upper side of squeezing gun that can be opened or closed in hinged mode after stopping squeezing viscous fluid in double cartridge.

BRIEF DESCRIPTION OF THE DRAWINGS

The above object and other characteristics and advantages of the present invention will become more apparent by describing in detail preferred embodiments thereof with reference to the attached drawings, in which.

DETAILED DESCRIPTION OF THE INVENTION

Figure 1:
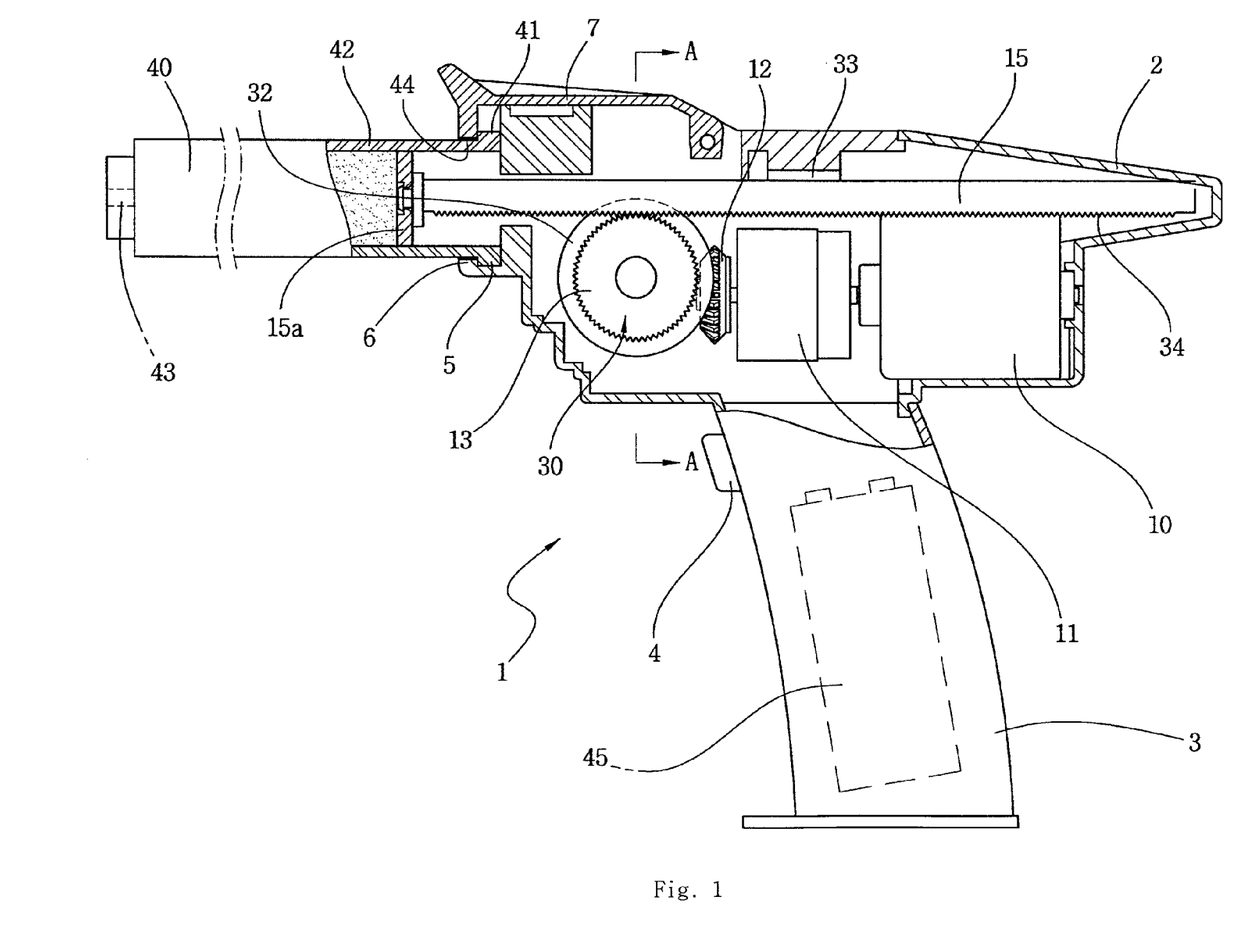
FIG. 1 refers to cross section that shows the first implementation of this invention.
Figure 2:
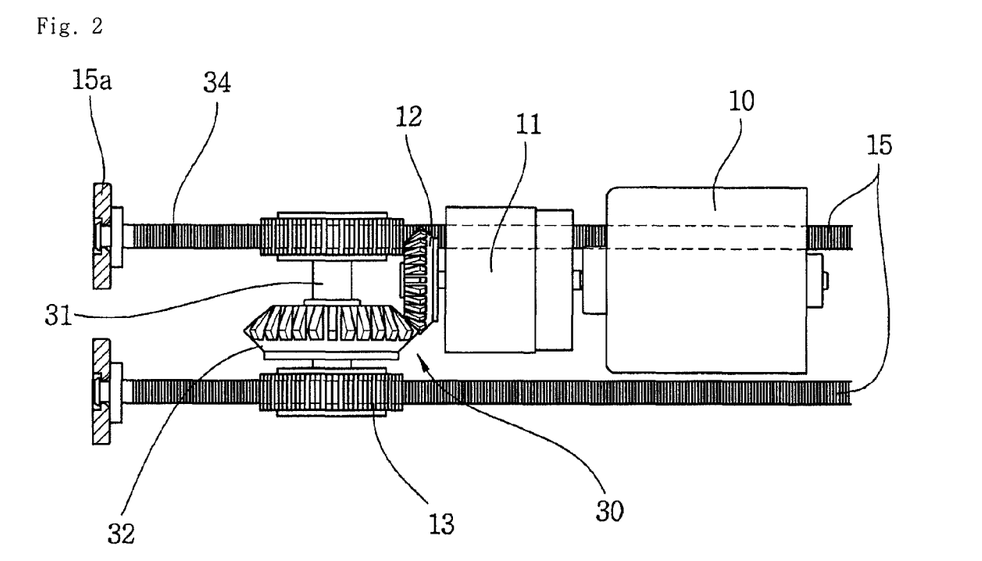
FIG. 2 refers to low section diagram which shows the state of installation of power delivery means and horizontal scroll bar which are installed in this invention.
Figure 10:
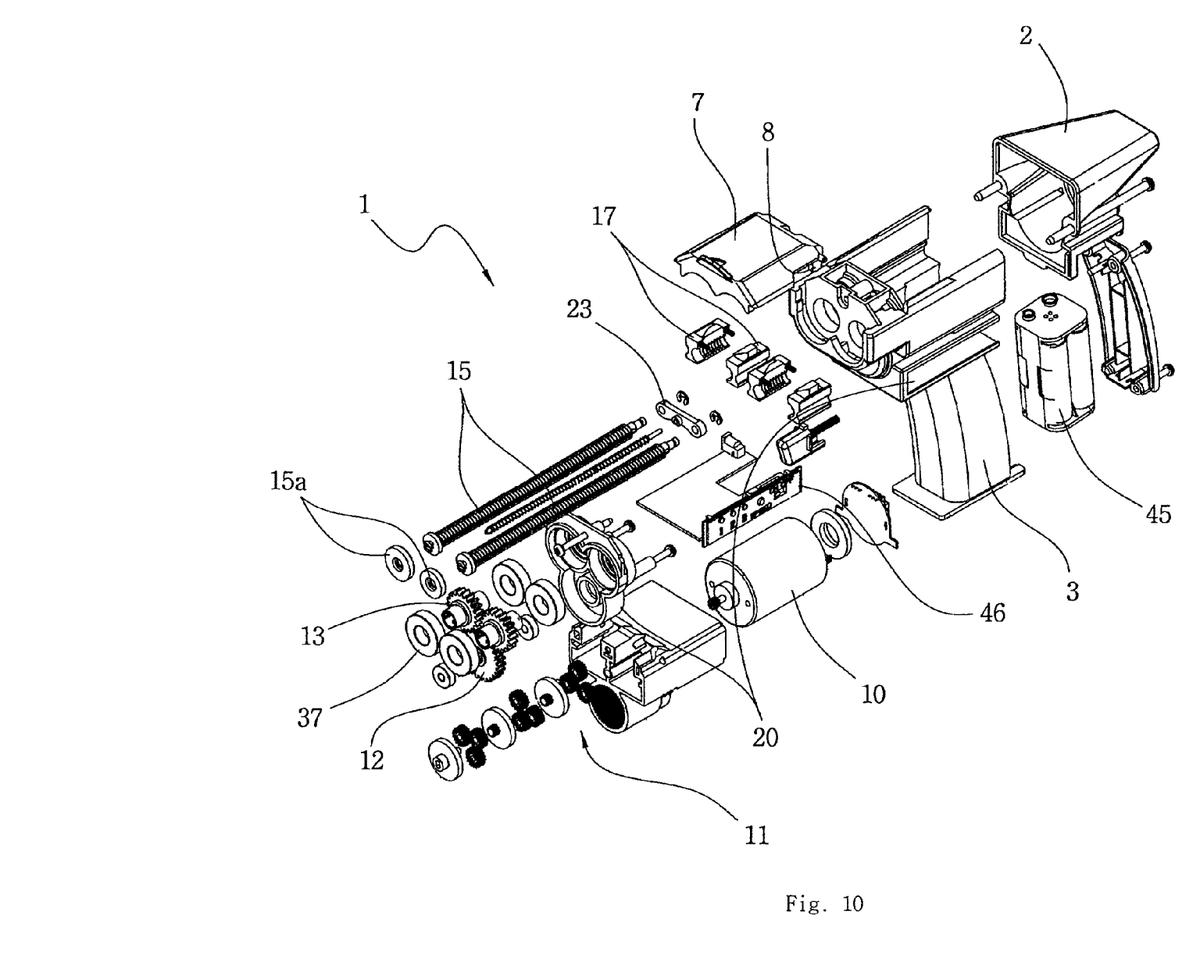
FIG. 10 refers to disassembly perspective view which shows the second implementation example.

Explanation of squeezing gun for two-part medical viscous fluid according to this invention referring to FIG. 1 and FIG. 10 is as follows.

This invention is to squeeze viscous fluid contained in double cartridge with the power of driving motor 10 by installing driving motor 10 on squeezing gun 1 which has the shape of pistol where double cartridge 40 is installed in removable mode.

Forward area of double cartridge 40 mentioned above is equipped with stout divider 43 and a pair of tubes 42 whose rear side is open is combined in one body and at the rear side of double cartridge where a pair of tubes are combined in one body, flange part 41 that is designed to install double cartridge 40 at the forward area of squeezing gun 1 in removable mode is formed protruded outward and in each tube 42 mentioned above, different kinds of viscous fluid is filled.

Figure 3:
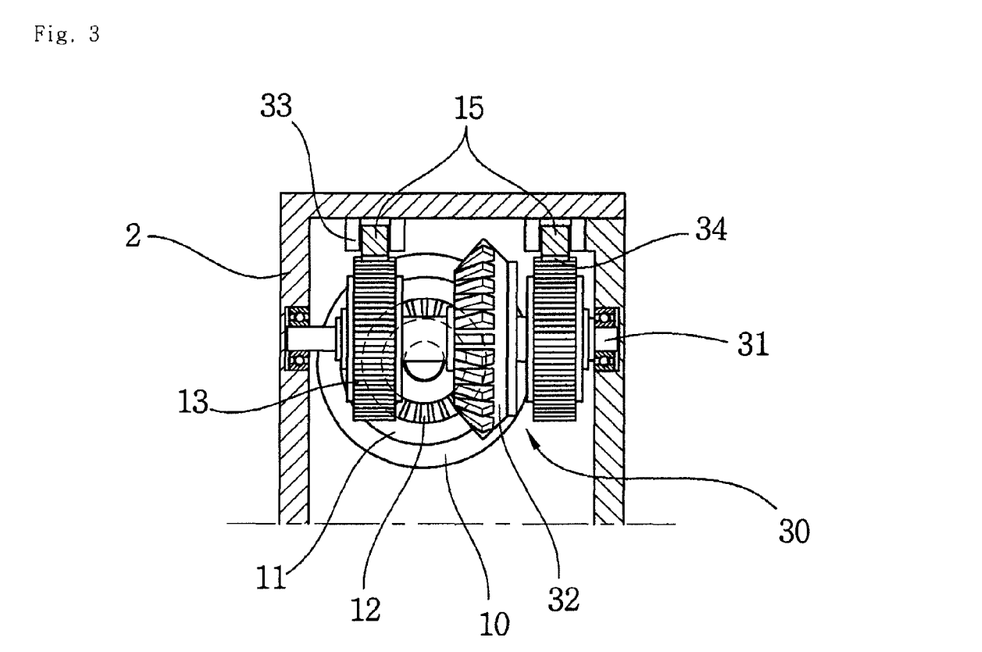
FIG. 3 refers to A-A line cross section of FIG. 1.

As shown in FIG. 1 and FIG. 3, case main body 2 whose forward are is open is installed on the upper side of handle 3 where push button is installed and cartridge insertion part 6 equipped with flange hanging hole 5 where flange part 41 of double cartridge 40 is inserted and hung is formed and a pair of horizontal scroll bars 15 that move forward horizontally by pressing push button 4 is installed inside of case main body 2.

Driving motor 10 equipped with decelerator 11 is installed inside of case main body 2 and driving gear 12 is installed in the axis of rotation of decelerator 11 and power delivery means 30 that deliver turning force of decelerator 11 to horizontal scroll bars of both sides 15 and make horizontal scroll bars move horizontally is installed between driving gear 12 and horizontal scroll bar 15.

Screw thread 34 is formed throughout the length of horizontal scroll bar 15 of power delivery means 30 and this screw thread 34 can be formed with screw bar shape but in the case of first implementation example of this invention, it is desirable that rack gear is formed throughout the lower length of horizontal scroll bar 15.

Intermediary gear 32 which engages driving gear 12 in the axis of rotation 31 which is installed freely and final gear 13 which engages screw thread 34 of horizontal scroll bar of both side 15 are installed inside of case main body 2 respectively.

Upper forward area of case main 2 is installed open so that cover 7 can be opened and closed and at the lower side of this cover 7, hanging part 44 that makes flange part 41 of double cartridge 40 is inserted and hung is formed when cover 7 is closed, and guide 33 that directs smooth horizontal movement of horizontal scroll bar 15 inside of case main body 2 of both sides.

Figure 4:
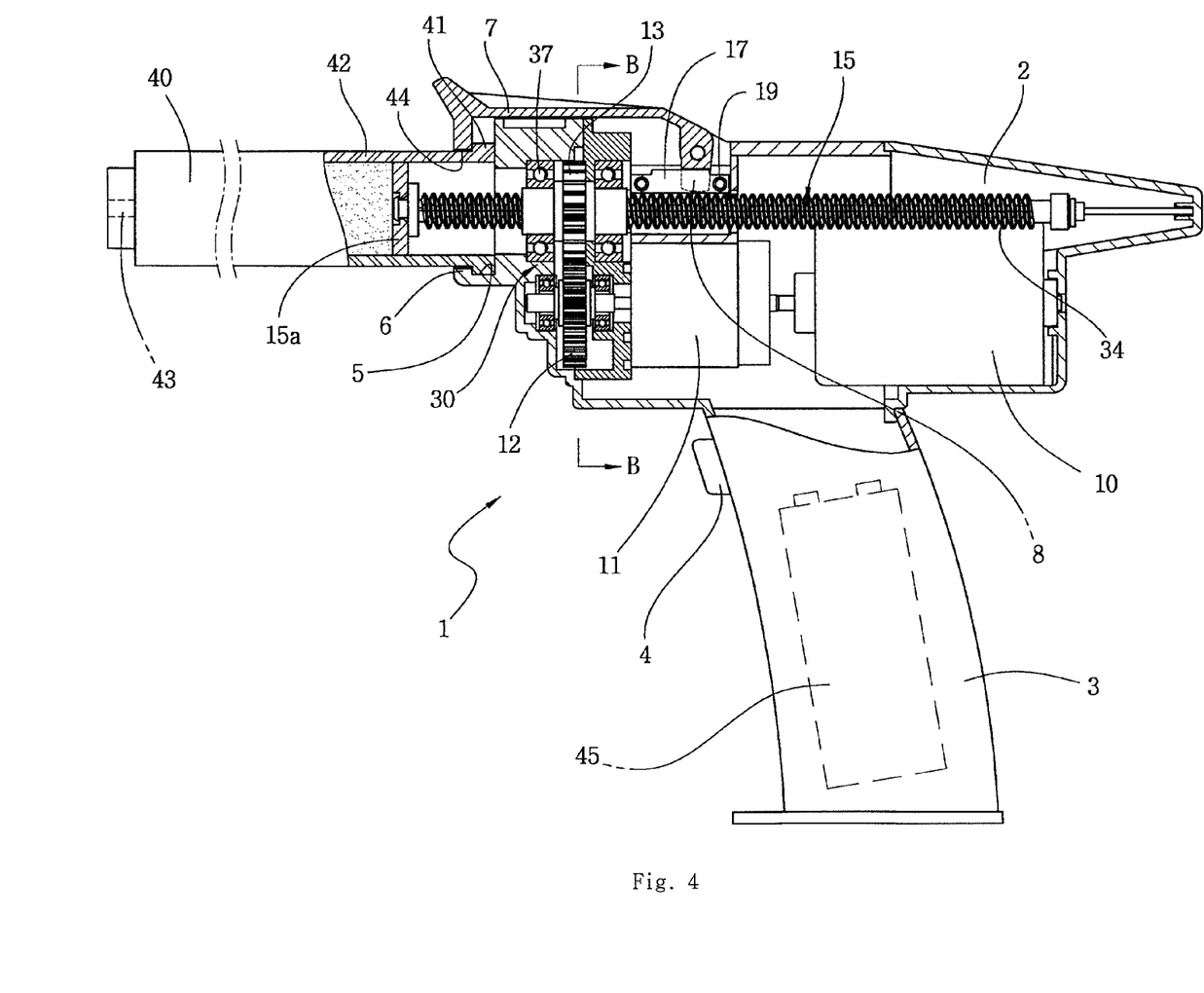
FIG. 4 refers to cross section which shows the second implementation example of this invention.

The following is about the second implementation example referring to FIG. 4 and FIG. 10 and in the case of the second implementation example, the way of squeezing viscous fluid contained in double cartridge 40 from squeezing gun 1 by the power of driving motor 10 equipped with double cartridge 40 is the same as that of the first implementation example.

With regard to squeezing gun 1 in the second implementation example, as shown in FIG. 4, case main body 2 whose forward area is open is installed on the upper side of handle 3 where push button 4 is set up and cartridge insertion part 6 equipped with flange hanging hole 5 where flange part 41 of double cartridge 40 is inserted and hung is formed at the open forward area of case main body 2 and a pair of horizontal scroll bars that move forward horizontally by pressing push button 4 is installed.

Driving motor 10 equipped with decelerator 11 is installed in the case main body 2 and driving gear 12 is installed in the axis of rotation of decelerator 11 and power delivery means 30 that enable horizontal scroll bars 15 to move horizontally by delivering the turning force of decelerator 11 to horizontal scroll bars 15 of both sides is installed between driving gear 12 and horizontal scroll bars (15).

Figure 5:
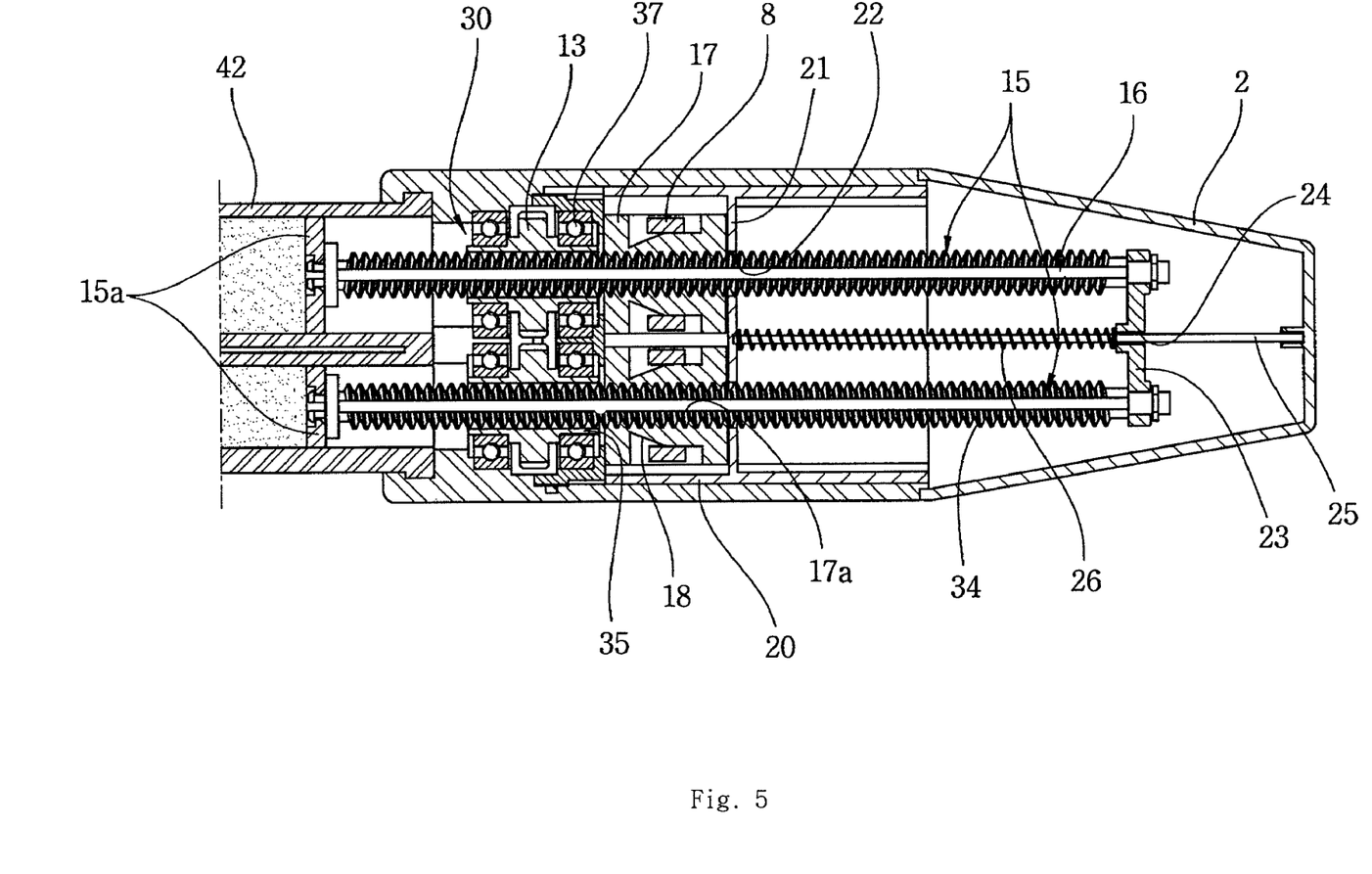
FIG. 5 refers to horizontal section which shows the state of installation of power delivery means and horizontal bar that is installed in this invention shown in FIG. 4.
Figure 6:
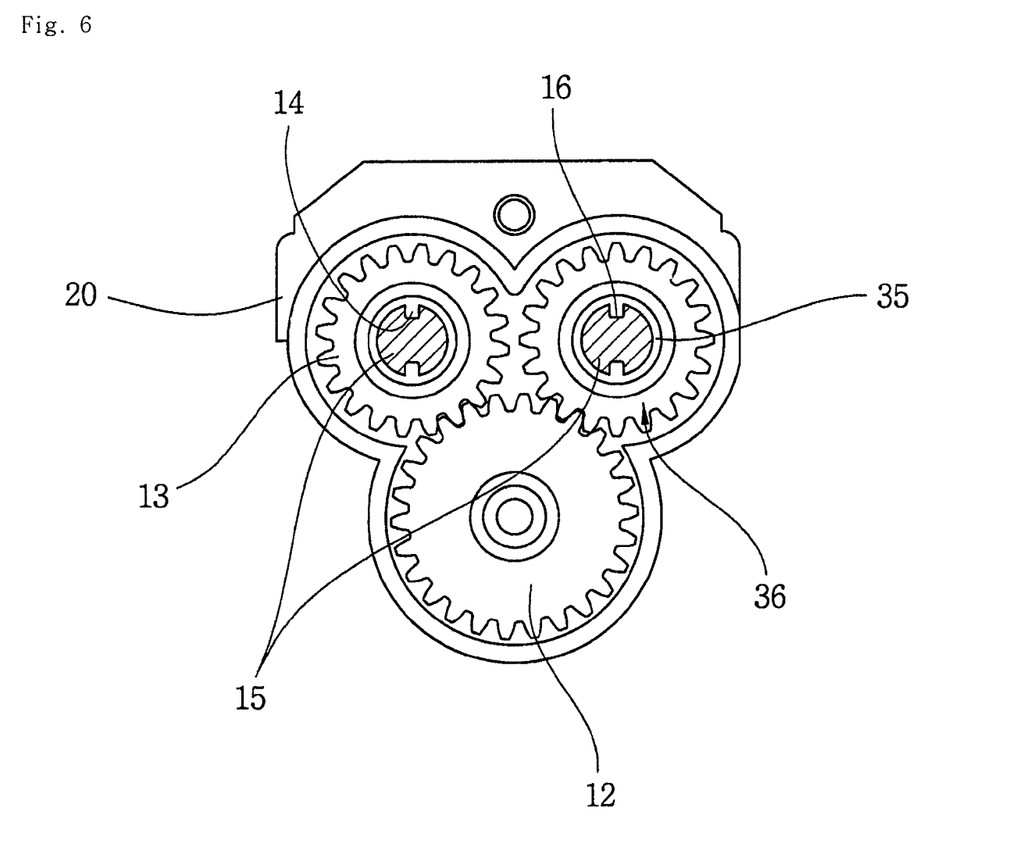
FIG. 6 refers to B-B line cross section of FIG. 4.

As shown in FIG. 5 and FIG. 6, with regard to power delivery means 30, screw thread 34 is formed throughout all outer circumferential edges of horizontal scroll bar 15 and key way 16 is formed throughout the length of horizontal scroll bar 15 in transverse direction.

A pair of horizontal scroll bars 15 pass through case main body 2 and housing 20 which driving gear 12 is exposed forward is installed and gear rotation body 36 which engages driving gear 12 is installed at both sides of housing 20 mentioned above and this gear body of rotation 36 is installed so that it can be moved straight by being inserted outside of horizontal scroll bar 15.

With regard to gear rotation body 36, protruded key 14 that is directed by being inserted into key way 16 of horizontal scroll bar 15 is formed in the tube type main body 35 and final gear 13 which engages driving gear 12 is formed at the center of circumference of tube type main body 35 is formed and outside of forward and backward of tube type main body 35 is inserted into the bearing 37 which is installed in housing 20 and consequently rotation is supported.

Figure 7:
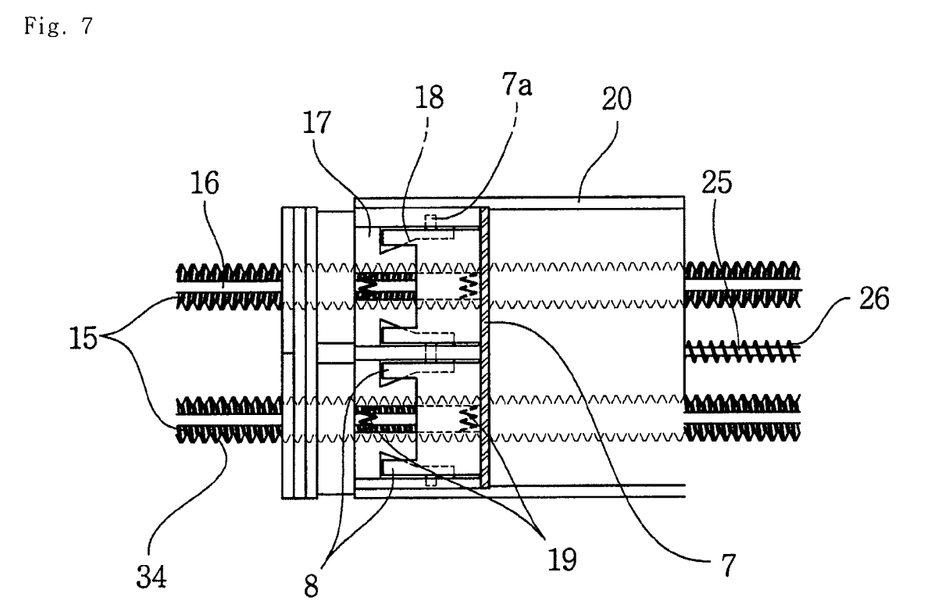
FIG. 7 refers to horizontal section which shows the state of installation of clutch that is installed in the second implementation example.
Figure 8:
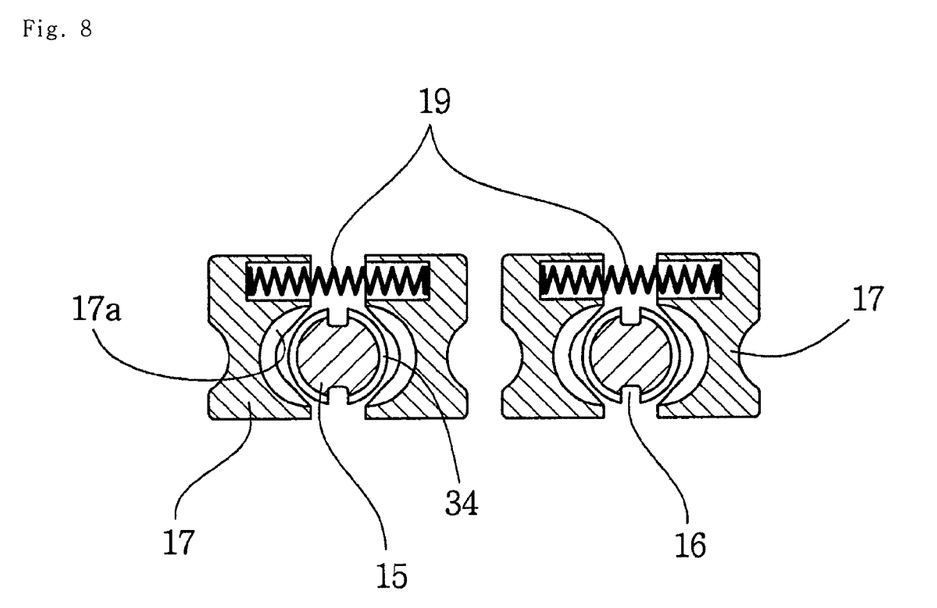
FIG. 8 refers to longitudinal section which shows the state of installation of clutch and horizontal scroll bar that are installed in the second implementation example.

As shown in FIGS. 5, 7 and 8, clutch 17 that makes horizontal scroll bar 15 of both sides move backward by spring 26 and makes horizontal scroll bar 15 moves horizontally in screw mode is installed on the horizontal scroll bar 15 of both sides in housing 20.

The clutches mentioned above are made up of a pair of clutch on left side and on the right side and screw way 17a that corresponds to screw thread 34 of horizontal scroll bar 15 is formed inside and slope part 18 is formed outside so that device can be pursed inward by being inserted into clutch purse part 8 and spring 19 that makes pursed a pair of clutches 17 stretched out is installed between a pair of clutches 17.

Cover 7 that covers the upper open side of housing 20 is installed on the upper forward open side of housing 20 by hinge pin 7a and clutch purse part 8 that makes a pair of clutches 17 pursed inward by being inserted outside of slope part 18 of clutches 17 of both sides when closing cover (7) is formed inside with "⊏"shape.

Figure 9:
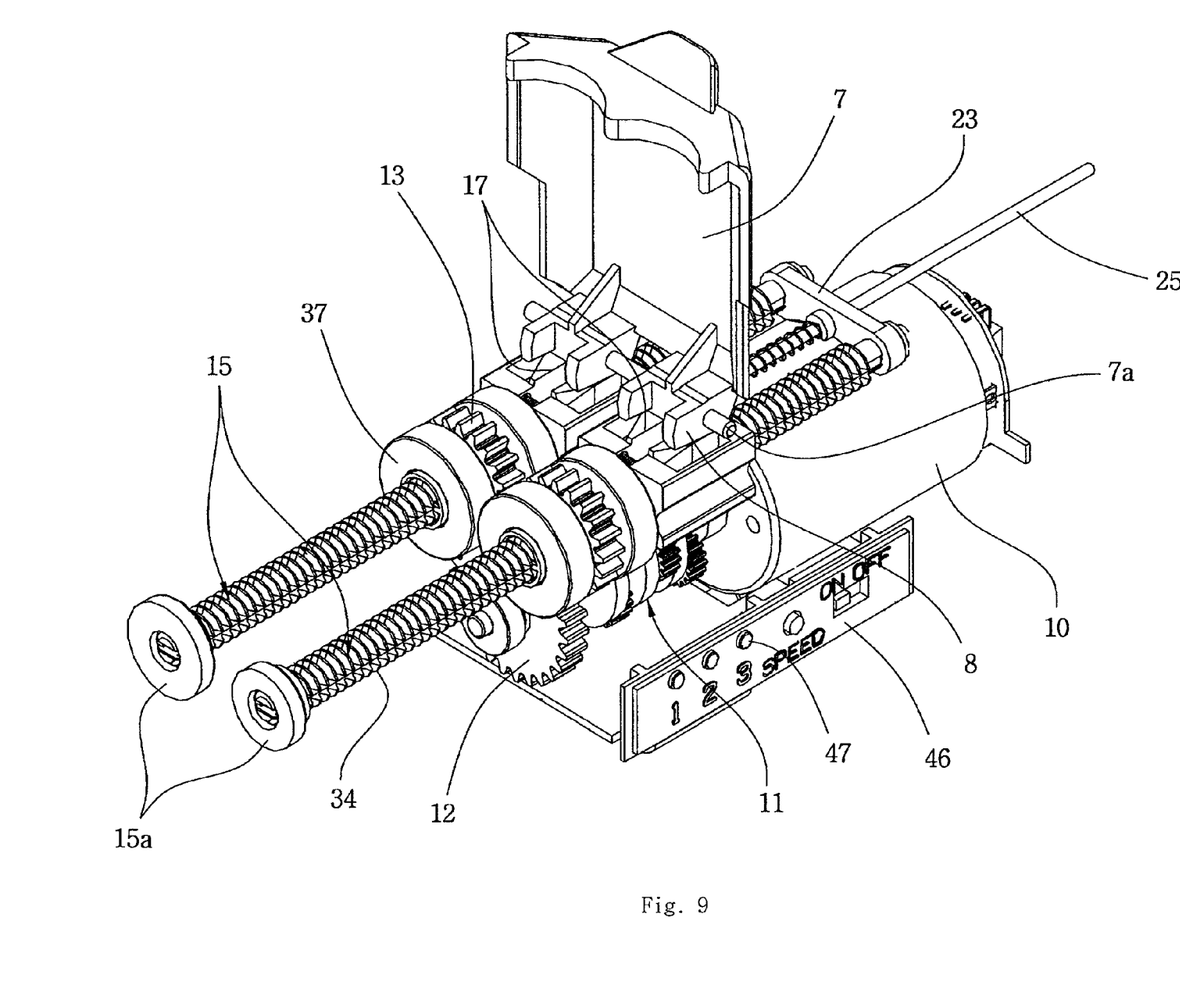
FIG. 9 refers to partial perspective view which shows main body of the second implementation example.

As shown in FIGS. 5 and 9, horizontal scroll bars 15 are protruded backward through holes 22 that are formed on the rear wall 21 of housing 20 and rear edge of horizontal scroll bars 15 of both sides that are protruded backward are installed so that it can be supported by bracket 23 and spring 26 that makes horizontal scroll bar 15 move backward is installed between rear wall 21 and bracket 23.

At this time, holes 24 are formed at the center of bracket 23 mentioned above and guide pin 25 penetrates holes 24 and the front edge of guide pin 25 supports the rear side of center of rear wall 21 and spring 26 mentioned above is installed elastically between rear wall 21 and bracket 23 while inserted into guide pin 25.

Decelerator 11 mentioned above is designed to decelerate the rotation of driving motor 10 and decelerator which uses super gear or decelerator which uses worm gear and as shown in FIG. 10, this invention has installed epicyclical gear as decelerator.

Supplying power to driving motor 10 can be possible by installing battery 45 in the handle 3 with removable mode and operating driving motor 10 with power supply of battery 45 and it is desirable that this battery 45 is charged by using additional charger.

Though I have not shown the example in a drawing, horizontal scroll bars of both sides of squeezing gun can be installed so that they can be moved forward and backward by using air pressure cylinder.

Interaction of this invention which is composed mentioned above can be explained as follows referring to FIGS. 1 and 10.

In the first implementation example shown FIGS. 1 and 3, after cartridge insertion part 6 is exposed to the forward area of case main body 2 by opening the cover 7 of squeezing gun 1, if flange part 41 of rear edge of double cartridge 40 inserts flange hanging way 5 and closes cover 7, rear flange part 41 of double cartridge 40 is inserted into flange hanging way 5 of cartridge insertion part 6 and double cartridge 40 can be installed in the forward area of case main body 40 as the upper side of flange part 41 is fixed in hanging part 44 that is formed to be cut downward on the bottom side of edge of cover 7.

In this state, in the case user intends to squeeze viscous fluid contained in double cartridge 40, user should turn switch of control part 46 on and press optional switch that chooses rotation speed of driving motor 10 and press push button 4 which is installed at the forward area of handle 4 and make driving motor 10 run.

In this case, push button 4 is equipped with switch that driving motor 10 can choose rotation in correct and reverse direction and user should press push button 4 so that horizontal scroll bar 15 can be moved forward when squeezing viscous fluid.

When driving motor 10 rotates in the direction that horizontal scroll bar 15 can be moved forward, rotation of driving motor 10 decelerates in decelerator which is installed at the forward area of driving motor 10 and by the turning force decelerated mentioned above, driving gear 12 that is installed on rotation axis of decelerator 11 becomes rotated.

If driving gear 12 rotates, intermediary gear 32 which engages driving gear 12 rotates, as final gear 13 which engages screw thread 34 which is formed with the form of rack gear at the lower side of horizontal scroll bar is installed on both sides of rotation axis 31 where intermediary gear 32, final gears 13 of both sides rotate by turning force of driving gear 12 mentioned above.

At this time, as driving gear 12 of both sides engage screw thread 34 of horizontal scroll bar 15 as mentioned above, horizontal scroll bars 15 of both sides move forward and front edge of each horizontal scroll bar 15 is inserted into tube of double cartridge 40 and different kinds of viscous fluid that is filled in tube of both sides is squeezed through holes 43 that are formed at the front edge of tubes of both sides.

Two kinds of viscous fluid that is squeezed from two tubes are blended in mixed delivery branch which is installed at the forward area of delivery branch which is formed at the front edge of two tubes and squeeze viscous fluid at the place that is targeted.

In the case viscous fluid mentioned above is used for dental impression material, hardening begins from the time two kinds of viscous fluid which is squeezed from damaged tooth from dental patient are blended in mixture delivery branch and while hardening for some time and shape that is intended to install dental prosthesis for damaged tooth is molded.

While viscous fluid which is contained in tubes of both sides is squeezed, push button 4 continues to be pressed and after viscous fluid is squeezed, stop the rotation of driving motor 10 by discontinuing pressing push button 4.

If push button 4 that is intended to rotate driving motor 10 in reverse direction is pressed, horizontal scroll bars 15 of both sides which have been inserted in tubes of double cartridge 40 get out.

After horizontal scroll bars 15 of both sides get out of tube of double cartridge, hitching of hanging part 44 which is applied to flange part 41 of double cartridge 40 is removed, and double cartridge 40 detaches from cartridge insertion part 6 of squeezing gun 1 by raising rear side of flange part 41 of double cartridge 40 from flange hanging way 5 of cartridge insertion part 6.

When double cartridge 40 is detached from squeezing gun 1, application medication work of viscous fluid using squeezing gun 1 of this invention is completed. This invention enables viscous fluid squeezed easily as viscous fluid which is contained in double cartridge 40 is squeezed by driving force of driving motor 10.

The following is explanation about squeezing viscous fluid by using the second implementation example shown in FIGS. 4 and 10, the way that is used in the second implementation example is the same as that of the first implementation example in this case. When double cartridge 40 is installed in squeezing gun 1, double cartridge 40 is installed in cartridge insertion part 6 by opening cover 7 and than closing cover 7. After turning power switch that is installed on control part 46 on, user chooses rotation speed of driving motor 10 by optional switch 47.

When closing cover 7 after installing double cartridge into cartridge insertion part 6, as shown in FIGS. 4, 7 and 8, clutches of both sides 17 are pursed inside by slope part 18 while open entrance of clutch purse part 8 which is formed with " ⊏ "shape on cover 7 is inserted outside of slope side 18 of clutch 17.

As clutches 17 of both sides are pursed, screw way 17a which is formed in clutch 17 and screw thread 34 which is formed in circumference of horizontal scroll bar 15 engage each other.

At this state, if push button 4 is pressed, driving motor 10 is operated and driving gear 12 which is installed on the rotation axis of decelerator 11 rotates by turning force which decelerates with decelerator 11.

If driving gear 12 rotates, final gear 13 which engages driving gear rotates as shown in FIG. 6. Because final gear 13 is formed in a body outside of tube type main body 35 inserted outside of horizontal scroll bar 15 and protruded key which is formed in the tube type main body 35 is inserted in key way 16 which is formed throughout the length of horizontal scroll bar 15, horizontal scroll bar 15 rotates as final gear 13 rotates.

While horizontal scroll bar 15 rotates, because screw way 17a of clutch 17 whose location is installed fixed in housing 20 engages screw thread 34 of horizontal scroll bar 15 as shown in FIGS. 5 and 7, horizontal scroll bars of both sides 15 move forward while rotating in screw mode.

The reason final gear rotates at the same place and horizontal scroll bar which is installed in tube type main body of final gear 13 can move forward while rotating with final gear 13 is that protruded key 14 which is pressed out inside of tube type main body 35 is directed to key way 16 that is formed throughout the length of horizontal scroll bar 15.

As pushing plate 15a that pushes viscous fluid by being inserted in tubes 42 of double cartridge 40 is installed at the front edge of horizontal scroll bar 15, horizontal scroll bar 15 moves forward while rotating and on the other hand pushing plate 15a does not rotate and it is inserted into tube 42 and consequently, different kinds of viscous fluid is squeezed through delivery branch 43 which is formed at the front edge of both tubes.

Squeezing two kinds of viscous fluid which is squeezed from two tubes at the targeted place and molding the form that is intended to install dental prosthesis hardening as time passes in the case that viscous fluid is used for dental impression material is similar to the explanation in the first implementation example.

While viscous fluid is squeezed which is contained in tubes of both sides, push button 4 continues to be pressed and after viscous fluid is squeezed, a user should stop rotation of driving motor 10 by discontinuing the pressing push button 4.

After squeezing of viscous fluid is finished, in order to detach double cartridge 40 from squeezing gun 1, when a user opens cover 7 that is installed on the upper side of case main body 2, as shown in FIGS. 5, 7 and 8, clutch purse part 80 which is formed with " ⊏ "shape at the lower side of cover 7 is raised toward the upper side.

Clutch purse part 8 which is raised toward the upper side is originally inserted outside of slope part 18 in clip mode and as cover 7 opens, clutch purse part goes upward and clutch purse part 8 is detached from the outside of clutch 17.

If clutch purse part 8 which is formed with " ⊏ "shape is detached from outside of clutch 17, interconnection between screw way 17a and screw thread 34 which is formed in clutch is removed as both clutches 17 are stretched out by elasticity.

Removing interconnection between screw way 17a which is formed in clutch 17 and screw thread 34 which is formed around circumference of horizontal scroll bar 15 means that holding horizontal scroll bar as clutch 17 is removed. At this time, as shown FIGS. in 5 and 9, spring is installed between rear wall 21 of housing 20 and bracket 23 which is installed at the rear edge of horizontal scroll bar 15 of both sides and by the elasticity of the spring, bracket 23 is moved backward.

As rear edge of horizontal scroll bar 15 of both sides is connected and installed in the bracket 23, when opening cover 7, holding state about horizontal scroll bar 15 is removed and this free state horizontal scroll bar 15 moves backward promptly by elasticity of spring 26.

Front edge of the spring 26 mentioned above is supported on the rear wall 21 of housing 20 and rear edge of the spring is inserted in guide pin 25 that penetrates the holes 24 of bracket 23 and enables horizontal scroll bar 15 of both sides to move backward smoothly.

After horizontal scroll bars 15 of both sides get out of tube 42 of double cartridge 40, double cartridge 40 can be detached from cartridge insertion part 6 of squeezing gun 1 by raising upward rear side flange part 41 of double cartridge 40 from flange hanging way 5 of cartridge insertion part 6.

As double cartridge 40 is detached from squeezing gun 1, medication work of this invention using squeezing gun 1 is completed. This invention enables viscous fluid squeezed evenly easily as viscous fluid contained in double cartridge 40 is squeezed by driving force of driving motor 10.

What is claimed is:

1. A squeezing gun for ejecting two-part medical viscous fluid from a front of the squeezing gun, comprising:

a case main body having an open front area formed by a cartridge insertion part, the case main body being situated at an upper side of a handle in which a push button is installed;

a double cartridge, in which a pair of tubes is included, each of which is filled with different viscous fluid, the double cartridge having a rear flange part inserted and fixed in the cartridge insertion part;

a gear housing disposed within the case main body;

a pair of horizontal scroll bars that move forward when the push button is pressed, the scroll bars being installed in the case main body, screw threads being formed around all outer circumference edges of the scroll bars, a key way being formed in each of the scroll bars throughout the length thereof and a portion of the scroll bars including a rear end portion thereof protruding backward through holes that are formed through a rear wall of the gear housing;

a bracket supporting the rear end portion of the scroll bars;

a spring biasing the scroll bars toward a rear of the gear housing, the rear of the gear housing being disposed rearwardly of the open front area of the case main body;

a guide pin installed between the rear wall and the bracket and supporting the spring;

a driving motor, equipped with decelerator, installed in the case main body, the push button being depressable to actuate the driving motor and decelerator so as to cause said forward movement of the scroll bars;

a driving gear installed on an axis of rotation of the decelerator, a front portion of the scroll bars extending beyond the case main body, the gear housing and the driving gear;

two respective gear bodies which engage the driving gear at respective sides of the gear housing;

two tubular main bodies through each of which a respective one of the scroll bars pass and on each of which a respective one of the gear bodies is mounted;

two final gears which engage the driving gear and each of which is installed on the circumference of a respective one of the tubular main body bodies;

screw holes which correspond to screw threads of the horizontal scroll bars formed at both sides of a portion of the scroll bars located in the gear housing;

a pair of clutches each of which has an inclined exterior portion and each of which comprises two parts biased away from each other by a clutch spring; and two clutch adhesion parts that close up the respective clutches, the clutch adhesion parts being hingedly installed in an open forward upper side of the gear housing.

* * * * *